United States Patent [19]
Klein et al.

[11] Patent Number: 5,382,685
[45] Date of Patent: Jan. 17, 1995

[54] PREPARATION OF O-SUBSTITUTED HYDROXYLAMMONIUM SALTS

[75] Inventors: Ulrich Klein, Limburgerhof; Ernst Buschmann, Ludwigshafen; Michael Keil, Freinsheim; Norbert Goetz, Worms; Horst Hartmann, Boehl-Iggelheim, all of Germany

[73] Assignee: BASF Aktiengesellschaft, Ludwigshafen, Germany

[21] Appl. No.: 131,615

[22] Filed: Oct. 5, 1993

[30] Foreign Application Priority Data

Oct. 5, 1992 [DE] Germany .............................. 4233333

[51] Int. Cl.⁶ ............................................ C07C 239/20
[52] U.S. Cl. ...................................................... 564/301
[58] Field of Search ........................................ 564/301

[56] References Cited

FOREIGN PATENT DOCUMENTS 0259850 3/1988 European Pat. Off. .

OTHER PUBLICATIONS

Organic Syntheses collective vol. 3 pp. 172–174 John Wiley & Sons, Inc.: New York (1955).
Chemical Abstracts, Zorina et al, "Method for the Synthesis of O–Carboxymethylhydroxylamine Hydrochloride", vol. 96, No. 17, Apr. 26, 1982, p. 696.

*Primary Examiner*—Peter O'Sullivan
*Attorney, Agent, or Firm*—Oblon, Spivak, McClelland, Maier & Neustadt

[57] ABSTRACT

O-substituted hydroxylammonium salts are prepared by hydrolysis of acetone oxime ethers with acid in the presence of an additive, removing acetone and water by distillation with the aid of the additive.

6 Claims, No Drawings

PREPARATION OF O-SUBSTITUTED HYDROXYLAMMONIUM SALTS

The present invention relates to a novel process for preparing O-substituted hydroxylammonium salts of the formula 1

$$R\text{—}O\text{—}NH_2 \cdot HX \quad (1)$$

where R is alkyl of 1 to 5 carbons, especially methyl, ethyl, propyl, 1-methylethyl, butyl, 1-methylpropyl, 1,1-dimethylpropyl, pentyl, 1-methylbutyl, 2-methylbutyl, 3-methylbutyl, 1-ethylpropyl or 2-ethylpropyl.

O-substituted hydroxylamines are known. They are important intermediates for preparing crop protection agents, drugs or fine chemicals.

Methods for synthesizing O-substituted hydroxylamines are disclosed in the literature. A review of these methods is given in Houben-Weyl, Methoden der organischen Chemie, Vol. 10.1, page 1186.

O-substituted hydroxylamines can be prepared by hydrolyzing O-substituted benzaldehyde oximes (Petraczek, et al., Ber. dtsch. Chem. Ges. 16, (1883) 823), O-substituted alkyl hydroximates (Werner et al., Ber. dtsch. Chem. Ges. 26, (1983) 1567, Ber. dtsch. Chem. Ges. 27, (1894) 3350, U.S. Pat. No. 4,965,390), O-substituted benzophenone oximes (Semper et al., Ber. dtsch. Chem. Ges. 51, (1918) 928), O-substituted hydroxamic acids (EP 306 936), U.S. Pat. No. 5,008,455) and O-substituted N-hydroxyurethanes (Winternitz et al., Bull. Soc. chem. Fr. [5], 1958, 664, DE 32 45 503) with mineral acid.

Another method is reaction of hydroxylamine-O-sulfonic acid with alcohols (EP 341 693).

None of these methods is suitable for industrial use because the yields are low and the hydrolyses must be carried out at high temperatures, to which there are objections on the grounds of safety because the initial compounds and products contain labile and energy-rich N-O bonds and may decompose violently.

The precursors required for the preparation by the described processes are in many cases elaborate to prepare and are often contaminated with N-substituted products. Hydrolysis therefore results in mixtures of N- and O-monosubstituted and N,O-disubstituted hydroxylamines.

An economic and somewhat safer process for industrial preparation of O-substituted hydroxylamines is therefore the known hydrolysis of O-substituted acetone oximes.

The acetone oxime ethers required as precursors can be prepared in good yields without contamination by N-alkylated products. The acetone oxime derivatives are reasonably stable.

Acetone oxime ethers can be hydrolyzed by refluxing with hydrochloric acid. Thus, Bernhard et al. (Liebigs Am. Chem. 257, (1890) 203) prepared benzyloxylamine hydrochloride in 50% yield. Borek et al. (J. Am. Chem. Soc. 58, (1936) 2020) synthesized carboxymethoxylamine hydrochloride in 50% yield and Holland et al. (J. Chem. Soc. 1948, 182) obtained diethylaminoethoxylamine by this method, but no yield of isolated product is reported. Brossi et al. (Heterocycles 20, (1983) 839) prepared 3-(2,4,5-trichlorophenoxy)propoxylamine hydrochloride in 47% yield by hydrolysis in ethanolic hydrochloric acid. The final products from the known processes are impure and must be purified by recrystallization. The yields are too low for industrial use.

Hydrolysis of acetone oxime ethers to O-substituted hydroxylamines and acetone is an equilibrium reaction, and the equilibrium is on the side of the oxime ethers.

The equilibrium can be shifted towards the required O-substituted hydroxylamines in a conventional way by removing one of the products present in the mixture at equilibrium. It is economically preferable to remove acetone from the mixture by distillation.

Thus, for example, the hydrolysis of acetone oxime O-carboxymethyl ether with aqueous hydrochloric acid with removal of acetone by distillation is described Ln Org. Synth., Coll. Vol. 3, page 172. The process gives a yield of only 66–72% and cannot be applied to the preparation of the compounds to be prepared according to the invention.

This is because hydrolysis of acetone oxime ethers which have low molecular weight substituents using aqueous mineral acids and shifting the equilibrium by removing acetone by distillation results in the acetone oxime ethers distilling out along with the acetone.

It is therefore necessary to use a large excess of acetone oxime ether for the reaction. If the hydroxylamine salt decomposes during the distillation, the residue from the distillation contains an ammonium salt, eg. ammonium chloride.

DE 3631071 describes a process for hydrolyzing acetone oxime ethers with hydrochloric acid which is also suitable for acetone oxime ethers with low molecular weight substituents. However, a complicated special apparatus is necessary for this. The reaction temperature of 70°–140° C. is objectionable on safety grounds because it is near the decomposition point of the O-substituted hydroxylamines, which is about 140° C.

It is an object of the present invention to find a process which can be carried out batchwise in a standard apparatus and is suitable for acetone oxime ethers with low molecular weight substituents.

We have found that this object is achieved by adding substances which are inert under the reaction conditions, and it is then possible to remove the acetone produced in the reaction from the mixture by distillation without the acetone oxime ether distilling out with the acetone.

Examples of such inert additives are aliphatic $C_5$–$C_{12}$-hydrocarbons such as pentane, hexane, heptane, isopentane, isohexane, isoheptane, cycloaliphatic $C_5$–$C_{12}$-hydrocarbons such as cyclopentane, cyclohexane, cycloheptane, aromatic hydrocarbons such as alkylbenzenes, eg. toluene, benzene, o-, m- and p-xylene, halobenzenes such as chlorobenzene, o-, m- and p-dichlorobenzene, alkoxybenzenes, petroleum ether and naphtha. In the process according to the invention, acetone oxime ethers with low molecular weight substituents are not distilled out of the reaction mixture, and the distillate comprises a mixture of acetone, additive, possibly acid and water.

It is therefore now possible to hydrolyze acetone oxime ethers without loss thereof. This results in a considerably higher yield and purity of the final products.

The usual procedure is as follows: the acetone oxime ether, an excess of aqueous mineral acid and the inert additive are mixed and then a mixture of acetone, inert additive, possibly acid and water are distilled out until the distillate no longer contains acetone, and the O-substituted hydroxylamine is isolated as salt or, where appropriate, as free base. Purification, eg. by recrystallization, is no longer necessary.

The reaction is generally carried out at from 0° to 100° C., preferably from 40° to 80° C. The process according to the invention is not objectionable on safety grounds because the temperature is sufficiently different from the decomposition points of the O-substituted hydroxylamines.

The mineral acids, eg. hydrochloric acid, hydrobromic acid, hydroiodic acid, sulfuric acid, are generally employed in at least equimolar amounts. They are normally used in an excess of 10–500%, preferably of 30–100%, based on the acetone oxime ether.

Water is generally used in an up to 100-fold molar excess based on the acetone oxime ether because it is not only a reactant but also important as solvent. A 5-100-fold, preferably a 5-10-fold, molar excess based on the acetone oxime ether is normally used.

The O-substituted hydroxylamines can be isolated in the form of their salts or, after addition of alkalis, as free bases.

If it is wished to isolate the salts, the excess water is removed, for example, by azeotropic distillation using the inert additive to result in a suspension of the salt in the inert additive, and the salt can be removed from the suspension by filtration.

If it is wished to isolate the O-substituted hydroxylamines as free base, the pH is adjusted to about 10 after the reaction is complete, and the volatile O-substituted hydroxylamines are isolated by distillation. Involatile O-substituted hydroxylamines are isolated by extraction and subsequent evaporation of the extract under reduced pressure.

It may be expedient for industrial purposes, eg. to increase the space/time yield, to stop the reaction before conversion is complete. It is advisable in this case to isolate the O-substituted hydroxylammonium salts in place of the hydroxylamines because the unreacted acetone oxime ether is then present in the filtrate together with the inert additive after the removal of the hydroxylammonium salt. The filtrate can be used for the next reaction.

METHOD 1

O-methylhydroxylamine hydrochloride, hydrolysis without additive (not according to the invention)

174 g (2 mol) of acetone oxime O-methyl ether and 296 g (3 mol) of concentrated hydrochloric acid are heated to 100° C. in a glass flask. Distillation is carried out using a column with a length of 30 cm and a diameter of 2.5 cm, which is packed with 5 mm glass rings, with a reflux ratio of 6 until the distillate no longer contains acetone.

The temperature inside the flask is 100°–110° C. The total distillate comprises 132 g of a mixture of 66.4% acetone, 14% water and 14.8% acetone oxime O-methyl ether. The distillate contains 15% of the acetone oxime O-methyl ether employed. The contents of the flask are subsequently evaporated to dryness under reduced pressure.

Yield: 57%, 112 g of 85% pure product

According to the $^1$H-NMR spectrum, the product contains 15% ammonium chloride.

Melting point: 116°–120° C.

METHOD 2

O-methylhydroxylamine hydrochloride, hydrolysis without additive (not according to the invention)

The synthesis is carried out as described in Method 1 but distillation is carried out under 250–150 mbar so that the temperature inside the flask is 75° C. The distillate contains 30% of the acetone oxime O-methyl ether employed.

Yield: 70%, 119 g

According to the $^1$H-NMR spectrum, the product contains no ammonium chloride.

Melting point: 149°–151° C.

EXAMPLE 1

Preparation of O-methylhydroxylamine hydrochloride, hydrolysis with additive (according to the invention)

750 ml of cyclohexane, 174 g (2 mol) of acetone oxime O-methyl ether and 296 g (3 mol) of concentrated hydrochloric acid are heated to 75° C. Distillation under the conditions described in Method 1 results, at a temperature of 75°–78° C. inside the flask and a distillate temperature of 52°–72° C., in a two-phase distillate:

Upper phase: 750 g comprising 11 0% acetone and 89.0% cyclohexane

Lower phase: 119 g comprising 31.3% acetone, 8.1% cyclohexane, 53.0% water and 7.7% hydrogen chloride.

A further 900 ml of cyclohexane are added during the distillation. The water is subsequently removed by azeotropic distillation with the cyclohexane, and the aqueous distillate weighs 100 g and is composed of 3.6% cyclohexane, 77.4% water and 17.6% hydrogen chloride. The residue from the distillation is filtered with suction to separate the precipitated O-methylhydroxylamine hydrochloride from the cyclohexane, and the solid is dried.

Yield: 90%, 150 g of product

Melting point: 148°–150° C.

Elemental analysis: Calculated: C 14.38, H 7.24 O 19.16 N 16.77 Cl 42.45% Found: C 14.4, H 7.3, O 19.2, N 17.0, Cl 42.3%

EXAMPLE 2

Preparation of O-ethylhydroxylamine hydrochloride (according to the invention)

202 g (2 mol) of acetone oxime O-ethyl ether are reacted and worked up as described for acetone oxime O-methyl ether in Example 1.

Yield: 89%, 173 g of product

Melting point: 110°–113° C.

EXAMPLE 3

Preparation of O-methylhydroxylamine hydrochloride, hydrolysis with additive (according to the invention)

174 g (2 mol) of acetone oxime O-methyl ether, 296 g (3 mol) of concentrated hydrochloric acid and 593 g of hexane are heated to 65° C. Distillation under the conditions described in Method 1 results, at a temperature of 64°–65° C. inside the flask and a distillate temperature of 48°–58° C., until the distillate no longer contains acetone, in a mixture of acetone, hexane and water. The remaining water is subsequently removed by azeotropic distillation with hexane. The residue from the distillation is filtered with suction to separate the precipitated O-methylhydroxylamine hydrochloride from the hexane, and the solid is dried.

Yield: 80%, 113 g of product

Melting point: 148°–151° C.

We claim:

1. A batchwise process for preparing O-substituted hydroxylammonium salts of the formula 1

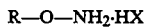

$$R-O-NH_2 \cdot HX \quad (1)$$

wherein R is $C_1$–$C_5$-alkyl and X is halogen or hydrogen sulfate, by reacting the corresponding acetone oxime ether of the formula 2

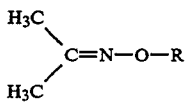

$$\begin{array}{c} H_3C \\ \phantom{H_3}\diagdown \\ \phantom{H_3C}C=N-O-R \\ \phantom{H_3}\diagup \\ H_3C \end{array} \quad (2)$$

with water and a mineral acid HX, wherein an inert substance selected from the group consisting of acyclic alphatic $C_5$–$C_{12}$-hydrocarbons, cycloaliphatic $C_5$–$C_{12}$-hydrocarbons, and unsubstituted or substituted aromatic hydrocarbons is added to the starting compounds, and the acetone produced in the reaction is removed by distillation without distilling out the acetone oxime ether together with the acetone.

2. A process as claimed in claim 1, wherein the reaction is carried out at 40°–80° C., and optionally the acetone is removed by distillation under reduced pressure.

3. A process as claimed in claim 1, wherein water is used in a 5-100-fold molar excess based on the acetone oxime ether.

4. A process as claimed in claim 1, wherein the mineral acid HX is used in a 30–100% molar excess based on the acetone oxime ether.

5. A process as claimed in claim 1, wherein, after complete removal of the acetone, the acid HX and water are removed together with the inert substance by azeotropic distillation, and the remaining O-substituted hydroxylamine is obtained as HX salt.

6. A process for preparing O-methyl- or O-ethylhydroxylammonium salts as claimed in claim 1, wherein acetone oxime O-methyl ether or acetone oxime O-ethyl ether is reacted with an aqueous mineral acid HX and an inert substance, the acetone produced in the reaction is removed by distillation together with the inert substance and water, and methoxylamine or ethoxylamine is isolated as salt by removing the remaining water and the remaining acid HX by azeotropic distillation with the inert substance, and the methoxylammonium salt or the ethoxylammonium salt is separated from the inert substance by filtering the residue from the distillation.

* * * * *